United States Patent [19]

Dobbs

[11] Patent Number: 5,129,822

[45] Date of Patent: Jul. 14, 1992

[54] DENTAL CASTING APPARATUS AND METHOD

[76] Inventor: Charles T. Dobbs, 18383 Van Rd., Livonia, Mich. 48152

[21] Appl. No.: 495,096

[22] Filed: Mar. 19, 1990

[51] Int. Cl.$^5$ .............................. A61C 19/00
[52] U.S. Cl. ...................................... 433/34
[58] Field of Search ........................ 433/34, 60, 74

[56] References Cited

U.S. PATENT DOCUMENTS

| | | | |
|---|---|---|---|
| 2,786,272 | 3/1957 | Lindley | 433/60 |
| 3,436,827 | 4/1969 | Dew | 433/34 |
| 3,495,333 | 2/1970 | Kuhn | 433/34 |
| 3,702,027 | 11/1972 | Marshall et al. | 433/34 |
| 4,300,884 | 11/1981 | Camacho | 433/74 |
| 4,508,506 | 4/1985 | Jackson | 433/74 |
| 4,767,330 | 8/1988 | Burger | 433/74 |
| 4,767,331 | 8/1988 | Hoe | 433/60 |
| 4,957,435 | 9/1990 | Jinoian et al. | 433/34 |

Primary Examiner—Gene Mancene
Assistant Examiner—Adriene B. Lepiane
Attorney, Agent, or Firm—Weintraub, DuRoss & Brady

[57] ABSTRACT

This dental casting apparatus includes a track, and a tray. The track has an inner and an outer track wall and a first and a second end portion which combine to define a chamber. A hardenable wet stone material is positionable within the chamber of the track. After the stone is allowed to harden within the track, a sharp knife cuts through the stone and the track to form a plurality of dies. The tray has an inner tray wall and outer tray wall which combine to define a recessed portion. The individual dies are positionable within the tray recessed portion, and are readily engageable and disengageable therefrom. The dental casting apparatus also includes a mechanism for securely retaining the dies to the tray in such a manner that each die can be individually removed from the tray without disengaging adjacent dies.

21 Claims, 3 Drawing Sheets

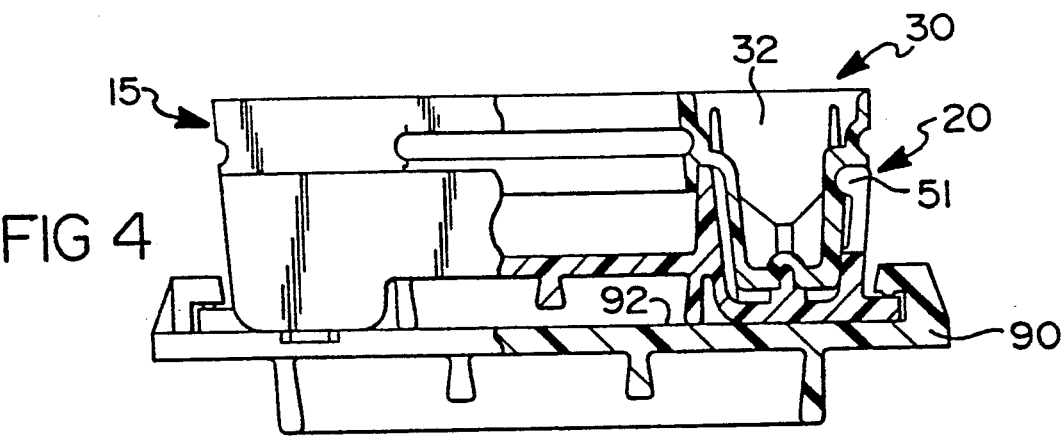
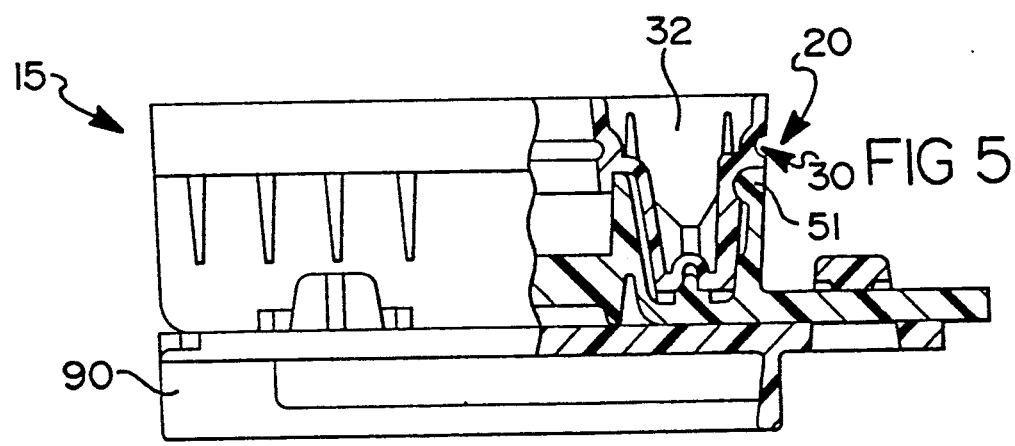
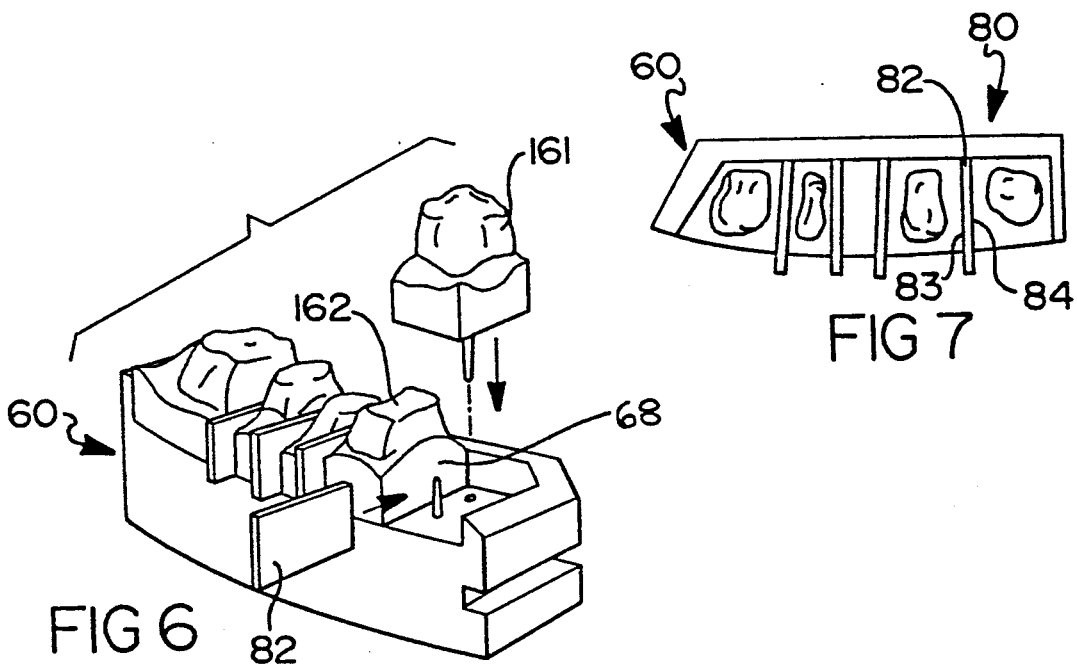

DENTAL CASTING APPARATUS AND METHOD

BACKGROUND OF THE INVENTION

1. Field of the Invention

The dental casting apparatus and method of the present invention involves a new apparatus and method for making one or more dies for crowns, bridges, and false teeth.

2. Background Art

The conventional system used in the United States for making dies for teeth is labor intensive. Initially, an impression of the patient's jaw is made and the impression is allowed to harden. The impression is then filled with wet stone, which must also be allowed to harden, forming a casting. The casting is then removed from the impression, a flat bottom portion and an outside wall for the casting are both formed by grinding out excess stone. An inside wall is formed for the casting by applying a lathe to remove excess stone. The casting is then cleaned by using pressurized air, and the casting is allowed to dry.

The individual pins are then drilled in the casting with a pindex machine: index pins are inserted and glued into a base for the casting, and doll pins are inserted into the upper portion of the casting. Typically the base is made from yellow stone, and the upper portion of the casting is made from green stone. A lubricant is then applied to the upper portion of the casting.

Recently, a new approach to making these dental castings has been developed, wherein the stone is embedded in a first member, which the first member is retained within a second member. These new systems use armatures disposed on the second member which cooperatively engage an undercut of the first member. The use of these armatures is limiting in that all of the dies must either be engaged or disengaged from the first member. There is no way to disengage only one die while the other dies remain firmly engaged.

In addition, if these new materials are reused for different patients, the accuracy of the dental castings made therefrom will diminish. Typically, the stone used to make the casting degrades over a period of time. As the stone wears, the stone chips and pieces become lodged within the various grooves of these members and are difficult to dislodge.

Also, most impressions are partial, and there may be no need to make a dental casting of an entire jaw. Current state-of-the-art makes no provision for a partial impression, as the patient must endure the discomfort of a full impression, and the dental technician must labor over a full impression when only one or two dies are needed.

Although these new dental casting systems are promising as far as eliminating much of the labor involved in making impressions, these materials are extremely expensive and the reduction in the labor costs are offset by increased equipment expenditures. Dental laboratories must continue to find new labor-saving techniques to reduce their costs, since the costs of labor and materials continue to rise, and it is difficult to pass these increasing costs along to the dentist and the patient.

What is needed is an apparatus to form a dental casting, the apparatus eliminating much of the labor in current techniques, the apparatus using materials that are inexpensive to manufacture, the materials being disposable after a single use, the apparatus enabling a partial impression to be made for the numerous instances when only one or two dies are needed, and the apparatus enabling a single die to be removed therefrom without disengaging neighboring dies therefrom.

SUMMARY OF THE INVENTION

The apparatus of the present invention overcomes the numerous shortcomings already mentioned, as is hereafter set forth.

The apparatus comprises a track and tray. The track has an inner and outer track wall and a first and a second end portion which combine to generally define a chamber. A hardenable stone material is embeddable within the chamber of the track. A plurality of individual dies are formed when the stone material hardens within the track to form a dental casting. As the stone and the track are sectioned to form a plurality of dies, each die includes a portion of the track. The tray has an inner tray wall and an outer tray wall which combine to generally define a recessed portion. The dies are positionable within the recessed portion, and the individual dies are readily engageable and disengageable therefrom.

The apparatus preferably includes cooperative retention means disposed on the track and the tray for securely retaining the dies of the dental casting system within the tray, in such a manner that any die can be individually removed from the tray without loosening an adjacent die.

The retaining means preferably includes a plurality of finger members disposed on the tray, the tray having a finger member for each die, as each die is secured by a different finger member. Each finger member includes a generally rounded portion. The outer wall of the lower member of each of the dies preferably has a rounded groove disposed therein. The rounded portion of each of the finger members snap-fits into the rounded groove of one of the dies.

For a more complete explanation of the dental casting apparatus and method of the present invention, reference is made to the following detailed description and accompanying drawings in which the presently preferred embodiments of the invention are illustrated by way of example. As the invention may be embodied in several forms without departing from the spirit or essential characteristics thereof, it is expressly understood that the drawings are for purposes of illustration and description only, and are not intended as a definition of the limits of the invention. Throughout the following description and drawings, identical reference numbers refer to the same components throughout the several views.

BRIEF DESCRIPTION OF THE DRAWINGS

FIG. 4 is a sectional view of the track positioned within the tray taken along section 4—4 of FIG. 3;

FIG. 5 is a sectional view of the track positioned within the tray taken along section 5—5 of FIG. 3;

FIG. 6 is an exploded perspective view of still another embodiment of the dental casting of the present invention, depicting a shim disposed between each pair of adjacent dies, the dies being individually secureable within the tray;

FIG. 7 is an overhead view of the dental casting of FIG. 6, with a shim disposed between each pair of adjacent dies;

DETAILED DESCRIPTION OF THE INVENTION

Figure 3:
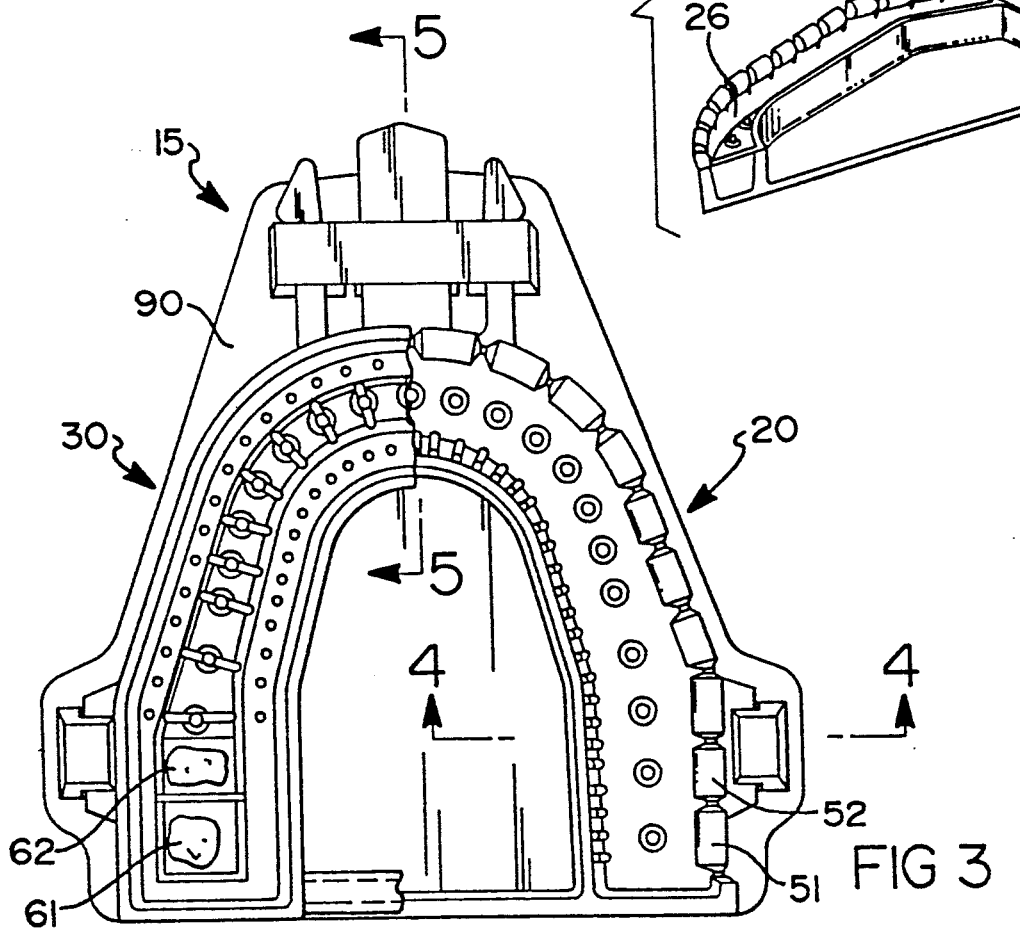
FIG. 3 is a cut-away overhead view of the dental casting apparatus of FIG. 1 depicting a half view of the track embedded within a half view of the tray.

Referring now the drawings, FIG. 3 depicts the preferred embodiment of the dental casting apparatus 15 of the present invention, which includes a tray 20, a track 30 which is positionable within the tray 20, and cooperative retention means 50 for retaining the track 30 within the tray 20.

The track 30 is preferably in the shape of a horseshoe, and includes a chamber 32. The chamber 32 is generally defined by an inner track wall 34 and an outer track wall 36, and a first end portion 33 and a second end portion 35. The chamber 32 is generally in the shape of the patient's jaw, or a portion thereof. The dental casting 60 of the hardened wet stone is disposed in the chamber 32. The dental casting 60 is formed from an impression of the patient's jaw, as is subsequently set forth herein. The hardenable wet stone material is well known in the art as conventional stone currently being used by dental laboratories. The dental casting 60 comprises a plurality of dies, including a first die 61 and a second die 62, the first die 61 being disposed adjacent to the second die 62 (see FIG. 3).

The track 30 preferably includes a stabilizer bar 38, the stabilizer bar 38 being an integral part of the track 30. The purpose of the stabilizer bar 38 is to minimize deformation of the track 30 when the wet stone hardens within chamber 32. The stabilizer bar 38 extends from the first end portion 33 to the second end portion 35. The stabilizer bar 38 maintains a fixed distance between the first end portion 33 and the second end portion 35 of the track 30 to prevent deformation thereof, enabling the track 30 to subsequently snap-fit into tray 20. The stabilizer bar 38 may be readily detached from the track 30, after the wet stone material hardens within the track 30, by using a pair of heavy duty clippers. The track 30 is preferably made of ABS plastic and is not reusable.

The tray 20 includes a recessed portion 26 surrounded by an inner tray wall 22 and an outer tray wall 24. The chamber 32 of the track 30 is positionable within the recessed portion 26 of the tray 20. The recessed portion 26 of the tray may be separated into a plurality of compartments 28, each compartment 28 retaining therein one die. The tray 20 preferably is of unitary construction, and is made of a flexible plastic material, such as ABS plastic, that may be formed by an injection molding process. The tray 20 is securely retained to a conventional articulator 90, which is used to simulate the movement of a human jaw. Plaster is preferably applied to the upper surface 92 of the articulator 90, and the tray 20 is subsequently positioned thereon (see FIGS. 3, 4, and 5). Preferably, the tray material is preferably more flexible than the track material, and the tray 20 is reusable. In actual practice, this is accomplished when the track 30 is filled with stone, causing the track material to lose some flexibility.

The dental casting apparatus 15 also includes a retaining means 50. The retaining means 50 enables the first die 61 to be readily disengaged from the tray 20 as the second die 62 is securely retained therewithin.

The retaining means 50 preferably involves a cooperative engagement between the track 30 and the tray 20. A first cooperative engagement member 39 may be integral with the track 30 and a second cooperative engagement member 51 may be integral with the tray 20. The cooperative engagement preferably is a plurality of snap-fittings 54, the number of snap-fittings 54 generally corresponding to the number of dies. A plurality of finger members, such as that shown at 51, are disposed within the tray 20. The first die 61 is retainable by a first finger member 71, the second die 62 is retainable by a second finger member 72, and so on. The first finger member 71 includes a generally rounded portion 55. The outer wall 36 of the track 30 has a rounded groove 39 disposed therein. The rounded portion 55 of each finger member snap-fits into the rounded groove 39 of the track 30. The first die 61 may be dislodged from the track 30 to retentively and removably lock the die into place in the track 30 by applying a grasping force thereto, the direction of which is away from the tray 20 to dislodge the rounded portion 55 from the groove 39.

Each die, as illustrated by the first die 61, comprises an upper member 65 and a lower member 66. The upper member 65 of the die is embedded to the lower member 66. A plurality of flexible retention pins 67 disposed on the track 30 are preferably, deflected into the stone when the wet stone is poured therein. When the stone material subsequently hardens within the track 30 the retention pins 67 extend into the upper member 65, and, thus, prevent the upper member 65 of the die from being separated therefrom. Accordingly, the upper member 65 is permanently embedded to plastic lower member 66.

Figure 1:
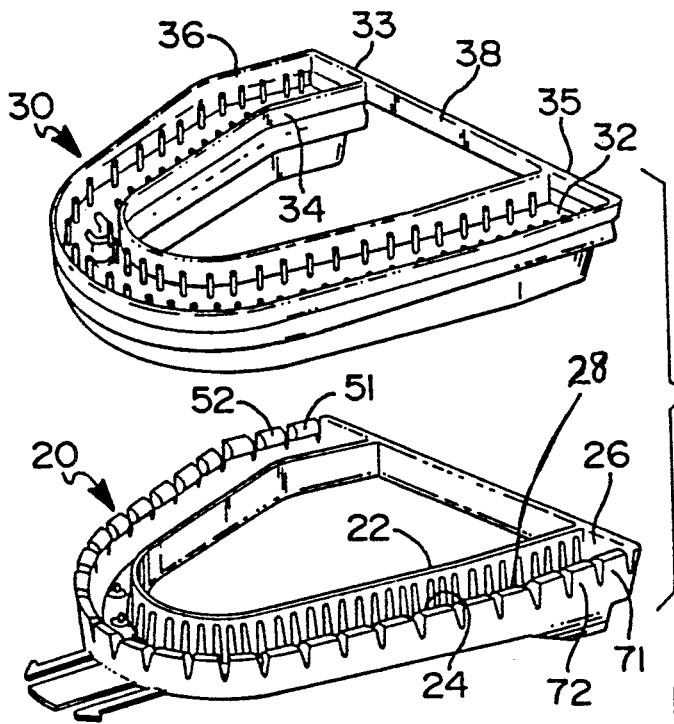
FIG. 1 is an assembly view of the preferred embodiment of the dental casting apparatus of the present invention depicting a track and a tray.
Figure 2:
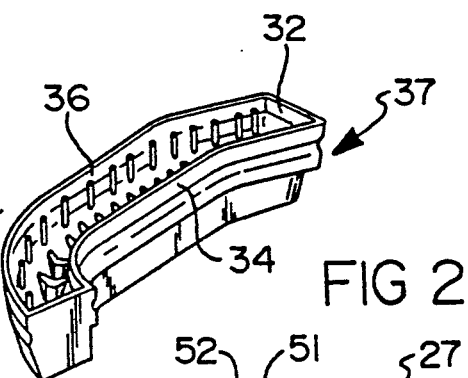
FIG. 2 is an assembly view of another embodiment of the present invention depicting a partial track and a partial tray.

The dental casting apparatus 15 is preferably available in an adult size and a children's size, the children's size being large enough to duplicate the jaw of a child, who is old enough to be acquiring a permanent set of teeth that may need to be crowned or replaced. The track 30 is preferably horse-shoe shaped as shown in FIG. 1. However, since 70 to 80 percent of all impressions are partials, the dental casting apparatus 15 may be similar in shape to a portion of patient's jaw, such as one-half of a jaw, and comprise a track-half 37 embedded within a tray half 27 (see FIG. 2).

Figure 8:
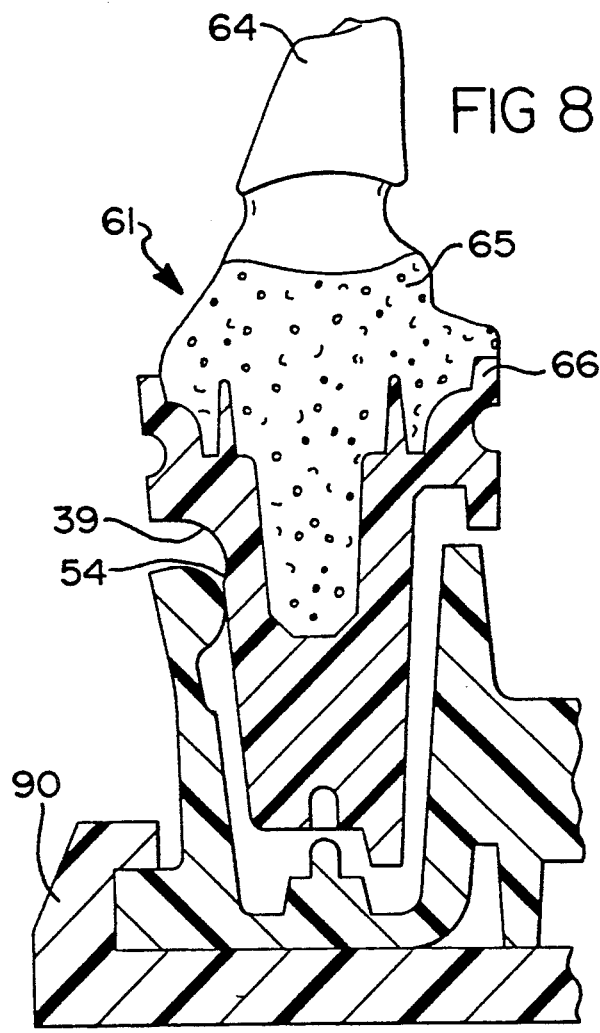
FIG. 8 is an exploded end sectional view depicting a die disengaged from the tray of FIG. 1.
Figure 9:
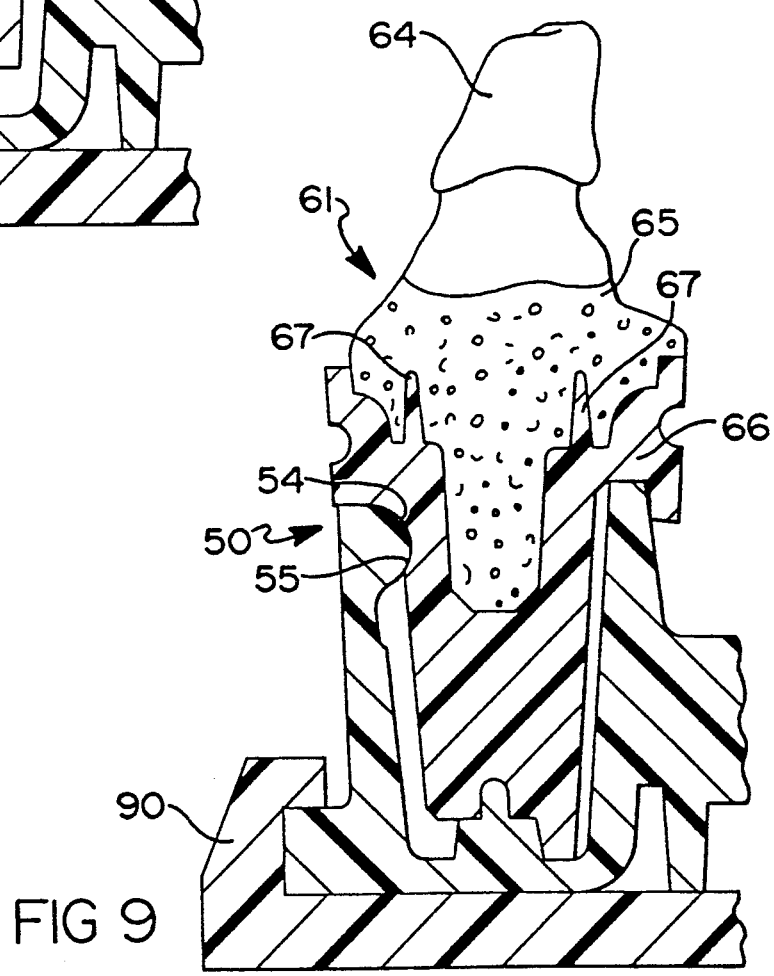
FIG. 9 is an exploded end sectional view depicting a die engaged within the tray of FIG. 8.

To remove a die 61 from the dental casting apparatus 15 of the present invention, the dental technician pulls the die 61 that is to be removed from the tray 20 (see FIGS. 8 and 9) away from the tray 20. As the rounded groove 39 is pulled away from the finger member 71, the die 61 is disengaged from the tray 20. As a result of the individual snap-fittings 54 between the individual dies 61 and the tray 20, the die 62, which is adjacent to the die 61 being removed, is securely retained within the tray 20. Similarly, to position the die 61 into the tray 20, the die 61 is initially aligned relative to the tray 20, and the die 61 is inserted into the tray 20 as the snap fitting 54 engages the die 61 and locks the die 61 into place.

To make a die of a tooth in accordance with the teachings of the present invention, an impression of the patient's mouth is initially made, and the impression is allowed to harden (not shown). The chamber of the impression is then filled with wet stone, as the chamber 32 in the track 30 is also filled with wet stone. The wet stone in the track 30 and wet stone in the impression are then aligned and joined together. The excess wet stone is trimmed and eliminated therefrom using a saw blade, and the wet stone is allowed to harden and the impression is removed from the dental cast 60. A saw blade penetrates through the hardened stone and the track 30, making a plurality of vertical cuts, preferably so that each die includes the shape of the upper portion of a single tooth. The individual dies are then assembled into the tray 20.

In an alternate embodiment, the retaining means 80 comprises a shim 82 that is positionable between each pair of adjacent dies 161, 162, as is shown in FIGS. 6 and 7.

The wet stone material is poured into the track 30, the track 30 being in the shape of either a full jaw or a portion thereof. The dental cast 60 comprises a plurality of dies positioned within the tray 20, and one or more shims 82 positioned between each pair of dies. The die 61 includes a portion 64 that is the shape of a portion of a tooth. Since the dies 61 and 62 are physically separated by the cutting edge of a saw blade (not shown), the cut is generally parallel to the axis of each die, and results in each die having a flat side portion 65. The dies are positionable within the track 30 in a location that is similar to the relative position of the teeth in the jaw of the patient.

Each shim 82 has opposed surfaces 83 and 84 which are generally flat, and the thickness of the shim 82 is essentially equal to the distance between the two flat surfaces 83 and 84. In this embodiment, the thickness of the shim 82 is ,also, generally equal to the distance between the first die 161 and the second die 162 when the first die 61 and the second die 62 are retained within the track 30. The thickness of the shim 82 is essentially equal to a kerf of the saw blade that physically separates the first die 61 from the second die 62. In actual practice, the thickness of the shim 82 is about one-ten thousandth of an inch less than the saw blade to enable the individual dies to be removed therefrom. Preferably, the two surfaces 83 and 84 of the shim 82 each have a tacky, self-adhesive material disposed thereon to adhere to the flat side portions 68 of the die between which the shim 82 is positioned within the track 30. To disengage a die 161 from the tray 20, the shim 82 connecting the first die 161 to an adjacent die 162 is pulled out and the die 161 is then removed. Adjacent dies still have a shim 82 on the opposite side thereof to securely retain them within the tray 20.

While the dental casting apparatus and method has been described in conjunction with specific embodiments, it is evident that many alternatives, modifications, and variations will be apparent to those skilled in the art in light of the disclosure therein. It is intended that the metes and bounds of the invention be determined by the appended claims rather than by the language of the above specification, and that all such alternatives, modifications, and variations which form a functional or conjointly cooperative equivalent are intended to be included within the spirit and scope of these claims.

I claim:

1. A dental casting apparatus comprising:
   (a) a first die and a second die, the first die having an upper member made of a stone-like material, the first die having a lower member made of a solid material, the stone-like material being embedded within the solid member, the first die being adjacent to the second die;
   (b) a tray, the tray having an inner tray wall and an outer tray wall, the inner tray wall and the outer tray wall cooperating to define a recessed portion therebetween, the first die and the second die being positionable within the recessed portion of the tray; and
   (c) means for retaining the first die and the second die to the tray, the retaining means comprising a plurality of snap-fittings, a first snap-fitting engaging the first die to the tray, and a second snap-fitting engaging the second die to the tray; the retaining means enabling the second die to be disengaged from the tray as the first die is securely engaged within the tray.

2. The dental casting apparatus of claim 1, wherein the tray has a unitary construction, the tray being made of flexible plastic material that is formable by injection molding.

3. The dental casting apparatus of claim 1, wherein the retaining means includes a first finger member and a second finger member, the finger members being formed as a part of the tray and extending upwardly thereon at one of the tray walls, the first die being retainable by the first finger member, the second die being retainable by the second finger member.

4. The dental casting apparatus of claim 3, wherein the first finger member includes a portion which extends inwardly thereon in the recessed portion of the tray, the first die having a groove disposed therein, the first finger member being flexibly movable and snap-fitting into the groove, the second finger being flexibly movable and snap-fitting into the groove.

5. The dental casting apparatus of claim 1, wherein the first die is disengageable from a first compartment of the tray by applying a grasping force to the first die in a direction away from the tray.

6. A track for making a dental cast from a wet-stone material, comprising:
   (a) an inner and an outer track wall and a first and a second end portion, the outer track wall having an external surface, the inner track wall and the outer track wall and the first and second end portion cooperating to define a chamber therebetween, the wet-stone material being disposable within the chamber, the chamber being separable into a first and a second compartment, the first compartment being suitable for forming a part of a first die, the second compartment being suitable for forming part of a second die;
   (b) means for disengagably locking and cooperatively retaining the first die and the second die to a tray, the cooperative retaining means enabling the second die to be disengaged from the tray as the first die is securely engaged within the tray, the cooperative retaining means comprising a plurality of snap-fittings between the track and the tray.

7. The track of claim 6, further comprising a stabilizer bar which extends from the first end portion to the second end portion, the stabilizer bar maintaining a fixed distance between the first end portion and the second end portion.

8. The track of claim 6, wherein the cooperative retaining means includes a rounded groove formed in the external surface of the outer wall, the rounded groove being cooperatively engageable with a first finger member of the tray to securely retain the first die therewithin while the second die is being removed therefrom.

9. The track of claim 6, wherein the first compartment is disengageable from the tray by applying a grasping force to the first compartment in a direction away from the tray, while the second compartment is securely retainable within the tray.

10. A tray for the secure retention of a first die and a second die, the tray comprising:
   (a) an inner and an outer tray wall, the inner and outer tray wall cooperating to define a recessed portion therebetween, the first die and the second die having a snap-fitting engagement within the recessed portion, the first die being securely retainable adjacent to the second die; and
   (b) means for cooperatively retaining the first die and the second die in fixed relation to the tray, the cooperative retaining means enabling the second die to be disengaged from the tray while the first die remains securely engaged with the tray, the retaining means being operable to temporarily and disengagably lock the first die and the second die in the tray.

11. The tray of claim 10, wherein the cooperative engagement means comprises a first and a second snap-fitting, the first snap-fitting being engageable with the first die, the second snap fitting being engageable with the second die.

12. The tray of claim 11, wherein the tray is of unitary construction, the tray being made of a flexible plastic material that is formable by injection molding.

13. A die that is generally flattened on opposing sides thereof, the die comprising:
   (a) an upper member made of a stone-like material, a portion of the upper member being similar in shape to a portion of a tooth; and
   (b) a lower member made of a solid material, the lower member having an external surface, the upper member being securely affixed to the lower member;
   wherein the lower member locks in and is retained to a tray by snap-fitting into the tray, and the die is removed from the tray by the application of pulling force thereto.

14. The die of claim 13, wherein the lower member has a cooperative snap-fitting engagement with a tray.

15. The die of claim 14, wherein the cooperative snap-fitting engagement comprises a rounded groove disposed on the external surface of the lower member.

16. A method of positioning a first die of a dental cast into a tray, the first die and a second die being securely retainable within the tray, the method comprising the steps of:
   (a) aligning the first die adjacent to a second die, the second die being positioned within the tray; and
   (b) snap-fitting the first die into the tray, while the second die is securely retained within the tray.

17. The method of claim 16, wherein the first die is lockably retained within the tray by the snap-fitting between the die and the tray.

18. The method of claim 16, wherein the first die comprises:
   an upper member made of a stone-like material; and
   a lower member made of a solid material, the lower member having an external surface, the lower member being securely affixed to the upper member, the external surface of the lower member having a snap-fitting engagement with the tray.

19. A method of forming a die, and locking the die into a tray, comprising the steps of:
   (a) providing a track, the track being made of a solid material, the track having disposed therein a chamber;
   (b) pouring a wet-stone material into the chamber;
   (c) allowing the wet-stone material to harden in the chamber;
   (d) making a plurality of slices through both the hardened stone material and the track material with a saw blade to form the die, the die including a stone portion and a track portion;
   (e) placing the die into a tray, the die having a first retaining portion and the tray having a second retaining portion;
   (f) snap-fitting the first retaining portion into the second retaining portion to lock the die within the tray.

20. The method of claim 19, wherein the wet-stone material is permanently embedded within the track.

21. An apparatus for use in forming dental castings, comprising:
   (a) a tray which is formed from a flexible plastic material, the tray having an inner wall and an outer wall, the inner and outer tray walls cooperating to define a recessed portion therebetween for receiving a track therein;
   (b) a track which is alignable with the tray and which at least partially fits within the recessed portion of the tray, the track having a chamber formed therein for receiving a casting material; and
   (c) means on the track for snap-fitting engagement with a portion of the tray to temporarily and disengagably lock the track, or a portion thereof, to the tray.

* * * * *